United States Patent [19]

Kleiner et al.

[11] Patent Number: 4,485,052

[45] Date of Patent: Nov. 27, 1984

[54] PROCESS FOR THE PREPARATION OF PHOSPHONOUS ACIDS

[75] Inventors: Hans-Jerg Kleiner, Kronberg; Hubert Neumaier, Brühl, both of Fed. Rep. of Germany

[73] Assignee: Hoechst Aktiengesellschaft, Frankfurt am Main, Fed. Rep. of Germany

[21] Appl. No.: 443,133

[22] Filed: Nov. 19, 1982

[30] Foreign Application Priority Data

Nov. 21, 1981 [DE] Fed. Rep. of Germany ....... 3146196

[51] Int. Cl.³ .............................................. C07F 9/48
[52] U.S. Cl. ................................ 260/502.4 R; 568/17
[58] Field of Search ................................ 260/502.4 R

[56] References Cited

U.S. PATENT DOCUMENTS

| 2,605,280 | 7/1952 | Klotz | 260/500 |
| 3,557,202 | 1/1971 | Stamm et al. | 260/502.4 R |
| 3,714,043 | 1/1973 | Clark | 260/502.4 R |
| 3,825,629 | 7/1974 | Hofer et al. | 260/502.4 R |
| 3,974,217 | 8/1976 | Miles | 260/502.4 R |

OTHER PUBLICATIONS

Frank, "Chem. Rev.", vol. 61, Aug. 1961, No. 4, pp. 389–395 and 419–424.
Chem. Abstracts, vol. 92, 1980, p. 687, Abstract No. 58894k.

*Primary Examiner*—J. E. Evans
*Attorney, Agent, or Firm*—Curtis, Morris & Safford

[57] ABSTRACT

Phosphonous acids are obtained by hydrolysis of dichlorophosphanes with water at temperatures of about 60° to about 100° C., preferably of about 80° to about 95° C.

9 Claims, No Drawings

PROCESS FOR THE PREPARATION OF PHOSPHONOUS ACIDS

Phosphonous acids are compounds of the general formula

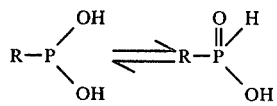

in which R=an organic radical.

Some of them are intermediates and some are end products in various specialized fields. Phosphonous acids are intermediates in the fields of, for example, flameproofing and plant protection, and end products in the fields of, for example, stabilizers and antistatic agents. For example, benzenephosphonous acid and its salts are valuable stabilizers for polyamides and the like.

Phosphonous acids can be prepared inter alia by hydrolysis of dihalogenophosphanes according to the equation below [Houben-Weyl, Methoden der organischen Chemie (Methods of Organic Chemistry), Volume XII/1 (1963), page 294]:

$R-PHal_2 + 2 H_2O \longrightarrow$

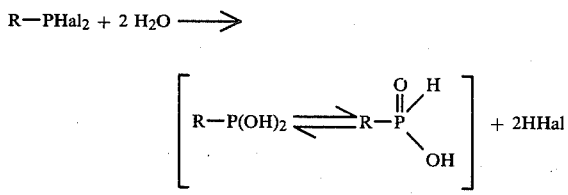

(Hal=halogen).

According to the literature reference cited, this reaction must be carried out under the mildest possible conditions—i.e. at room temperature or at a temperature only slightly above it—because the phosphonous acids formed in the reaction are said to disproportionate at elevated temperatures into the corresponding phosphonic acids and the (foul-smelling and poisonous and hence exceptionally undesirable) primary phosphanes; the disproportionation is based on the following equation:

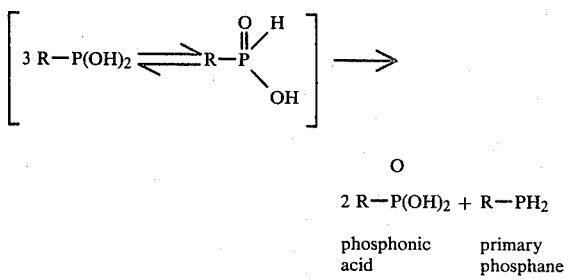

$2 R-P(OH)_2 + R-PH_2$ phosphonic acid    primary phosphane

In the example given in the abovementioned literature reference for the preparation of chloromethyl-phosphonous acid by hydrolysis of chloromethyl-dichlorophosphane (dropwise addition of the chloromethyl-dichlorophosphane to concentrated hydrochloric acid), the reaction temperature is given as 20°-30° C., the mixture subsequently being stirred for a short time at 50° C. After the water and hydrochloric acid have then been distilled off in vacuo, 99% of theory of chloromethyl-phosphonous acid is said to remain.

The example gives no indication of the possible formation of phosphonic acid and phosphane (by disproportionation of the chloromethyl-phosphonous acid).

The fact that disproportionation of the phosphonous acids is not absent, or not entirely absent, even at the customary low reaction temperatures for the hydrolysis of dihalogenophosphanes to the corresponding phosphonous acids, is apparent, for example, from the article by G. M. Kosolapoff and J. S. Powell in J. Amer. Chem. Soc. 72 (1950), page 4,291. The experimental part of this article reports an experiment involving the "conventional hydrolysis" of phenyldichlorophosphane—i.e. supposedly hydrolysis of the phenyldichlorophosphane at room temperature or at a temperature only slightly above it—and the resulting, exceptionally foul smell of the phenylphosphane; this is a result of which the Applicant Company has also been able to provide full confirmation by means of its own experiments.

Because the hydrolysis of halogenophosphanes to the corresponding phosphonous acids is otherwise not uneconomical, however, it was an object of the invention to improve this reaction further so that disproportionation of the phosphonous acids no longer occurs.

It was possible to achieve this object, according to the invention, by the use of a higher reaction temperature than that which was customary in the past.

The subject of the invention is therefore a process for the preparation of phosphonous acids by hydrolysis of dichlorophosphanes (also called phosphonous dichlorides or dichlorophosphines) with water; the process comprises carrying out the hydrolysis at temperatures of about 60° to about 100° C., preferably of about 80° to about 95° C.

It is exceptionally surprising that the disproportionation of the phosphonous acids is completely absent, or in any case virtually completely absent, in this temperature range, because, according to Houben-Weyl, loc. cit., an increased disproportionation was to be expected under these very conditions.

In principle, any possible dichlorophosphanes can be used as starting materials for the process; however, it is preferred to use dichlorophosphanes of the formula $R-PCl_2$, in which R=$C_1$-$C_{18}$-alkyl, especially $C_1$-$C_4$-alkyl, $C_7$-$C_{12}$-aralkyl, especially benzyl, or $C_6$-$C_{10}$-aryl, especially phenyl.

The dichlorophosphanes can be obtained in a known manner, for example by reaction of alkanes, preferably methane, or of benzene with phosphorus trichloride at about 600° C. (German Offenlegungsschrift No. 2,046,314, German Pat. No. 2,629,299), or by reaction of chlorobenzene with phosphorus trichloride and phosphorus at 300°-350° C. (German Offenlegungsschrift No. 2,452,582). The water used for the hydrolysis is advantageously in excess. The excess should be at least 10%. Excesses of up to about 300% can also be of technical advantage. Higher excesses are not necessary.

The process is carried out in a simple manner by metering the dichlorophosphane into the water already present, at about 60° to about 100° C., preferably at about 80° to about 95° C., with stirring. The evolution of the hydrogen chloride gas formed in the course of the reaction begins after a certain time which depends on the temperature chosen and the amount of water used.

To avoid the high exothermicity (heat of solution of the hydrogen chloride formed) frequently occurring at the start of the reaction, which permits only a low metering rate of the dichlorophosphane at the start of the reaction or requires cooling of the reaction vessel, it is also possible, in place of (pure) water, to start with concentrated hydrochloric acid in an amount which provides the necessary amount of water for the reaction.

It proved particularly favorable, in this reaction, to use a mixture of concentrated hydrochloric acid and part of the reaction product from a previous batch, still containing hydrogen chloride. In this case, the dichlorophosphane can be metered in a uniform stream without cooling the reaction vessel.

The process can be carried out either batchwise or continuously.

In both cases, however, the reaction is preferably carried out under an inert gas atmosphere, examples of possible inert gases being nitrogen, argon and/or carbon dioxide.

After the reaction has ended, the hydrogen chloride still present in the reaction mixture is removed in a conventional manner, together with the excess water, for example batchwise by distillation in vacuo or by stripping with the aid of an inert gas, or continuously in a heated stripping column under reduced pressure and/or in counter-current to an inert gas.

The phosphonous acids obtained by the process according to the invention contain only very small amounts—if any—of phosphonic acids and also, if appropriate, of phosphorous acid, which originates from slight oxidation of the starting dichlorophosphanes (→phosphonic acids) and also from contamination thereof by phosphorous trichloride (→phosphorous acid).

Because the procedure according to the invention avoids the disproportionation of the phosphonous acids, the invention represents a considerable improvement to the known hydrolysis of dihalogenophosphanes and thus represents a significant advance.

The invention is now illustrated in greater detail by means of the following examples. The phosphonic acids and phosphorous acid obtained in small amounts as by-products in the examples of the invention originate from slight oxidation of the starting dichlorophosphanes and also from slight contamination thereof by phosphorous trichloride. In contrast to the comparison example following the resulting of the invention (hydrolysis of phenyldichlorophosphane under customary conditions, i.e. at temperatures up to at most about 50° C.), in no case could the smell of phosphanes be detected.

EXAMPLE 1

473 g of 99% pure dichloro-methyl-phosphane are added dropwise to 180 g of water over a period of 4 hours, at 85°–95° C., under a nitrogen atmosphere and with stirring. At the start of this process, the dropwise addition is initially very slow. After 15 minutes, the evolution of hydrogen chloride starts. The gas evolved during the whole reaction is free of methyl-phosphane. After the reaction has ended, the mixture is cooled. This gives 408 g of a reaction solution containing 14% of hydrogen chloride. A water-pump vacuum is now applied and the hydrogen chloride is substantially removed, together with the excess water. The internal temperature is gradually increased to 95° C. during this process. After six hours, this gives 322 g of methylphosphonous acid with a residual content of 1.5% of hydrogen chloride. The product is a low-viscosity, colorless and odorless liquid. On the basis of a $^{31}P$ NMR spectrum, it contains 0.7% of methylphosphonic acid and 0.3% of phosphorous acid. The yield is about 100% of theory.

EXAMPLE 2

282 g of concentrated hydrochloric acid (36% strength) containing 180 g of water are heated to 85° C. under a nitrogen atmosphere. The source of heat is removed and 470 g of 99.7% pure dichloro-methyl-phosphane are metered in at a rate of 160 g/hour, it being possible to keep the reaction temperature initially at 85° C. After about 30 minutes, the reaction vessel must be heated again in order to maintain the reaction temperature of 85°. After the dropwise addition has ended (3 hours), the mixture is cooled. The reaction mixture, which still contains 17.4% of hydrogen chloride and the excess water, is passed continuously, over a period of 2 hours, through a stripping column heated to 100° C., at 4–5 kPa and in counter-current to about 35 liters/hour of nitrogen. This gives 321 g of methylphosphonous acid, which still contains 1.1% of hydrogen chloride and, on the basis of a $^{31}P$ NMR spectrum, contains 0.1% of methylphosphonic acid and 0.1% of phosphorous acid. The yield is about 100% of theory.

EXAMPLE 3

A mixture of 282 g of concentrated hydrochloric acid and 130 g of crude methylphosphonous acid (containing 17.4% of hydrogen chloride and 7% of water), the latter originating from a previous batch, is heated to 85° C. 470 g of 99.7% pure dichloro-methyl-phosphane are uniformly added dropwise over a period of 3 hours, the reaction vessel remaining in the heating bath throughout the addition.

Working-up as described in Example 2 gives 419 g of methylphosphonous acid, which still contains 1% of hydrogen chloride and, on the basis of a $^{31}P$ NMR spectrum, contains 0.1% of methylphosphonic acid and 0.15% of phosphorous acid. With regard to the amount initially present, the yield is about 100% of theory.

EXAMPLE 4

300 g of dichloro-ethyl-phosphane are added dropwise to 103 g of water over a period of 2.5 hours, at 90° C., under a nitrogen atmosphere and with stirring. The evolution of hydrogen chloride starts after 30 minutes. The gas evolved during the whole reaction is free of ethylphosphane. After the reaction has ended, the mixture is cooled. The reaction solution obtained still contains 13.8% of hydrogen chloride. Further working-up is carried out as in Example 1. This gives 215 g of ethylphosphonous acid with a residual content of 0.7% of hydrogen chloride. The product is a colorless and odorless liquid. On the basis of a $^{31}P$ NMR spectrum, it contains 0.8% of ethylphosphonic acid, 0.5% of phosphorous acid and 0.3% of phosphoric acid. The yield is about 100% of theory.

EXAMPLE 5

360 g of dichloro-phenyl-phosphane are added dropwise to 180 g of water over a period of 2.5 hours, at 95° C., under a nitrogen atmosphere and with stirring. The evolution of hydrogen chloride starts after about 30 minutes. The mixture is subsequently stirred for 1 hour at 90° C. and then cooled. The aqueous reaction solution still contains 11.9% of hydrogen chloride. The hydrogen chloride is removed in a water-pump vacuum, together with the excess water, up to an internal temperature of 80°–100° C. This gives 280 g of benzenephosphonous acid containing 0.8% of benzenephosphonic acid ($^{31}$P NMR spectrum). The yield is about 98.5% of theory.

COMPARISON EXAMPLE 360 g of dichloro-phenyl-phosphane are added dropwise to 180 g of water over a period of 2.5 hours, under a nitrogen atmosphere, without heating and with stirring. The smell of phosphanes appears after a short time. The temperature rises initially to a maximum of 50° C. The evolution of hydrogen chloride then starts and the temperature drops. The aqueous reaction solution obtained still contains 14.9% of hydrogen chloride. Working-up is carried out as in Example 3. This gives 280 g of benzenephosphonous acid containing 2.2% of benzenephosphonic acid ($^{31}$P NMR spectrum). The smell of phosphanes, together with the 1.4% higher phosphonic acid content—relative to Example 5 of the invention, which is to be compared with the present example—show that disproportionation of the benzenephosphonous acid has really taken place in this case.

When the same batch was treated with cooling, the amounts of phenylphosphane which evolved were driven out of the apparatus by the stream of nitrogen and were so large that the reaction was stopped prematurely.

We claim:

1. A process for the preparation of a phosphonous acid which comprises contacting dichlorophosphane with a reagent consisting essentially of water at a temperature of about 60° to about 100° C., wherein the dichlorophosphane is hydrolyzed according to the reaction

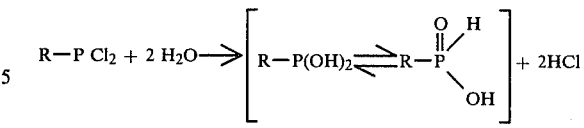

wherein R is an organic radical and maintaining the temperature at about 60° to about 100° C. throughout the course of the hydrolysis.

2. The process as claimed in claim 1, wherein the dichlorophosphanes are compounds of the formula $$R\text{—}PCl_2$$

in which R is $C_1$–$C_{18}$-alkyl, $C_7$–$C_{12}$-aralkyl, or $C_6$–$C_{10}$-aryl.

3. The process as claimed in claim 1, wherein, after the hydrolysis has ended, the hydrogen chloride formed and still present in the reaction mixture is removed.

4. The process defined in claim 2, wherein, after the hydrolysis is complete, hydrogen chloride formed and still present in the reaction mixture is removed.

5. The process, as claimed in claim 1, wherein the hydrolysis is carried out at a temperature of about 80° to 95° C. and the water temperature is about 80° to about 95° C.

6. The process, as claimed in claim 1, wherein in addition to water, the hydrolysis is carried out in the presence of hydrochloric acid or hydrochloric acid and a phosphonous acid, the amount of water being sufficient to carry out the hydrolysis.

7. The process, as claimed in claim 6, wherein the water is present in an excess amount of 10% up to about 300%, the hydrolysis is carried out at a temperature of about 80° to about 95° C., the water temperature is about 80° to about 95° C. and R is $C_1$–$C_{18}$-alkyl, $C_7$–$C_{12}$-aralkyl or $C_6$–$C_{10}$-aryl.

8. The process, as claimed in claim 7, wherein R is $C_1$–$C_{14}$-alkyl, benzyl or phenyl.

9. The process as claimed in claim 1, wherein R is $C_1$–$C_4$-alkyl, benzyl, or phenyl.

* * * * *